United States Patent [19]
Morris, Jr. et al.

[11] Patent Number: 5,258,284
[45] Date of Patent: Nov. 2, 1993

[54] NUCLEIC ACID PROBES SPECIFIC FOR PATHOGENIC STRAINS OF VIBRIO VULNIFICUS AND METHOD EMPLOYING THE SAME

[75] Inventors: J. Glenn Morris, Jr.; Anita Wright, both of Baltimore, Md.

[73] Assignee: University of Maryland, School of Medicine, Baltimore, Md.

[21] Appl. No.: 643,303

[22] Filed: Jan. 22, 1991

[51] Int. Cl.$^5$ ............................................. C12Q 1/68
[52] U.S. Cl. ..................................... 435/6; 536/24.32; 435/909
[58] Field of Search ....................... 435/6, 909; 536/27

[56] References Cited

PUBLICATIONS

Yamamoto, K. et al., (1990) Infect. Immun. 58(8), 2706–2709.
Morris, J. G., et al. (1987) Appl. Environ. Microbiol. 53(1), 193–195.
Wright, A. C., et al, (1985) Infect. Immun. 50(3), 922–924.

*Primary Examiner*—Charles L. Patterson, Jr.
*Attorney, Agent, or Firm*—Sughrue, Mion, Zinn, Macpeak & Seas

[57] ABSTRACT

Nucleic acid probes specific for pathogenic stains of *vibrio vulnificus* and methods employing the same, comprising nucleic acid hybridization probes specific for the vvh gene of pathogenic strains of *vibrio vulnificus*.

46 Claims, 1 Drawing Sheet

FIG. 1

SEQ ID NO:1:

CGCCACACGA GACTGGTGTA ATGC     24

SEQ ID NO:2:

GAGCTGTCAC GGCAGTTGGA ACCA     24

FIG. 2

SEQ ID NO:3:

CGCCACACGA GACUGGUGUA AUGC     24

SEQ ID NO:4:

GAGCUGUCAC GGCAGUUGGA ACCA     24

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGCCACACGA GACTGGTGTA ATGC    24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GAGCTGTCAC GGCAGTTGGA ACCA    24

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:3:

CGCCACACGA GACUGGUGUA AUGC 24

( 2 ) INFORMATION FOR SEQ ID NO:4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:4:

GAGCUGUCAC GGCAGUUGGA ACCA 24

NUCLEIC ACID PROBES SPECIFIC FOR PATHOGENIC STRAINS OF VIBRIO VULNIFICUS AND METHOD EMPLOYING THE SAME

The development of the present invention was supported by the University of Maryland and the U. S. Food and Drug Administration (contract #223-84-2031).

FIELD OF THE INVENTION

The present invention relates to nucleic acid hybridization probes specific for pathogenic species of *Vibrio vulnificus* and methods for employing the same.

BACKGROUND OF THE INVENTION

*Vibrio vulnificus* (*V. vulnificus*) is an estuarine bacterium that has been associated with severe wound infections or septicemia, particularly in immunocompromised individuals and in persons with conditions such as cirrhosis or hemochromatosis (Blake et al, *New Engl. J. Med.*, 300:1-5 (1979); and Klontz et al, *Ann. Intern. Med.*, 109:318-323 (1980)). Over 50% of persons with septicemia die, and one-third present with shock (Klontz et al, *Ann. Intern. Med.*, 109:318-323 (1980)). The mortality rate among patients who are hypotensive within 24 hours of hospital admission exceeds 90% ((Klontz et al, *Ann. Intern. Med.*, 109:318-323 (1980)). Three-quarters of the patients with septicemia have characteristic bullous skin lesions ((Blake et al, *New Engl. J. Med.*, 300:1-5 (1979) ; and Klontz et al, *Ann. Intern. Med.*, 109:318-323 (1980)) with histological findings compatible with a toxin-medicated process (Pollack et al, Arch. Intern. Med., 143:837-838 (1983)).

A cytolysin that is lytic for both erythrocytes and Chinese hamster ovary (CHO) cells has been isolated from culture supernatants (Kreger and Lockwood, *Infect. Immun.*, 33:583-590 (1981)). The purified protein has an estimated molecular mass of 56 kilodaltons (kDa). Although *V. vulnificus* produces both a phospholipase $A_2$ and a lysophospholipase, these enzymes have been shown to be physically separable from the cytolysin by gel filtration (Testa et al, *Infect. Immun.*, 45:458-463 (1984)). The toxin may bind cholesterol and has been shown to induce the release of $K^+$ ions, and to a lesser extent $Na^+$ ions, from liposomes (Yamanka et al, *FEMS Microbial. Lett.*, 44:253-258 (1987)). Other investigators have reported a possible second hemolysin with an estimated molecular mass of 36 kDA, whose hemolytic activity is neutralized by a monoclonal antibody that binds a 36-kDA protein, but not a 56-kDA protein in culture supernatants (Okada et al, *J. Gen. Microbial.* , 133:2853-2857 (1987)). However, the biological properties of both of these proteins appear to be identical, and the relationship between them is unclear.

Previously, the putative gene for *V. vulnificus* cytolysin were subcloned on a 3,4-kilobase (kb) insert in pBR325 and designated pCVD702 (Wright et al, *Infect. Immun.*, 50:922-924 (1985)). Both hemolytic and CHO cell-cytotoxic activities were expressed in *Escherichia coli*, and these activities were neutralized by antisera to the purified 56-kDa cytolysin. This DNA was shown to be specific for *V. vulnificus* and did not hybridize with DNA from other Vibrio or non-Vibrio species under stringent conditions.

However, homology was demonstrated for all clinical and environmental isolates of *V. vulnificus* examined, including pathogenic strains (Morris et al, *Appl. Environ. Microbial.*, 53:193-195 (1987)).

To date, practically and commercially suitable nucleic acid probes, specific for pathogenic strains of *V. vulnificus*, are not known in the art and there has been a need to provide a means to detect and/or diagnose humans or animals infected with pathogenic strains of *V. vulnificus*. The above-mentioned 3.4-kb subcloned fragment is not suitable for practical or commercial use since testing using this probes requires the use of a sophisticated molecular genetics laboratory, due the need to isolate this relatively large (3.4 kb) fragment from a plasmid immediately prior to each test. Additionally, such a probe requires labeling prior to each test, since such probes cannot be stored for extended periods of time due to loss of labeling.

Accordingly, there is a need to provide an nucleic acid probe specific for pathogenic strains of *V. vulnificus* which: can be suitably used without the need for a sophisticated molecular genetics laboratory; can be made inexpensively; does not require the use of labeling immediately prior to each test or require the use of radioactive probes; and can be labeled with non-radioactive probes.

SUMMARY OF THE INVENTION

Accordingly, it is an object of the present invention to provide commercially and practicably suitable nucleic acid probes that are specific and sensitive for pathogenic strains of *Vibrio vulnificus.*

Another object of the present invention is to provide nucleic acid hybridization probes comprising RNA or DNA which are specific for pathogenic strains of *V. vulnificus*, and which bind to a portion of the cytotoxin-hemolysin gene (*vvh* gene) of *V. vulnificus*. A further object of the present invention is to provide a method for detecting vvh DNA or RNA in an unknown sample of DNA or RNA, particularly an unknown sample of DNA or RNA from a human or animal, or from an environmental sample, so as to detect the presence of pathogenic strains of *V. vulnificus.*

In the context of the present invention, the term "sample" refers to an original sample or a cultured sample that is suspected to have pathogenic strains of *V. vulnificus.*

An even further object of the present invention is to provide nucleic acid probes which are specific for pathogenic strains of *V. vulnificus*, and which bind to a portion of the cytotoxin-hemolysin gene ( vvh gene) of *V. vulnificus* and that are between 15 and 200 bases in length, preferably between 15 and 50 bases in length, and more preferably between 15 and 30 bases in length.

Another object of the present invention is to provide nucleic acid probes that comprise sense and/or antisense nucleic acid sequences corresponding to a portion of the *vvh* gene, which are highly specific and sensitive for the *vvh* gene, and therefore specific for pathogenic strains of *V. vulnificus.*

An additional object of the present invention is to provide a method to detect pathogenic strains of *V. vulnificus* in a sample by providing a method for detecting i the presence of pathogenic strains of *V. vulnificus* in a sample comprising an unknown nucleic acid, comprising hybridizing (a) nucleic acid probes that comprise sense and/or antisense nucleic acid sequences corresponding to a portion of the cytotoxin-hemolysin gene (vvh gene)

which are highly specific and sensitive for the vvh gene, to (b) the unknown nucleic acid, and assaying for cross-hybridization between the probes and the unknown nucleic acid.

Thus, in one embodiment, the above-described objects of the present invention have been met by a DNA or RNA (complimentary to the vvh gene sense or antisense DNA or RNA) which has been labelled with a detectable marker.

In another embodiment the above-described objects of the present invention have been met by providing a nucleic acid hybridization probe specific for pathogenic strains of *Vibrio vulnificus*, wherein the probe:

(a) consists of a total nucleotide sequence of from about 15 to 200 bases in length; wherein at least 15 bases of the total nucleotide sequence corresponds to a polynucleotide sequence selected from the group consisting of SEQ ID NO: 1; SEQ ID NO: 2; SEQ ID NO: 3; and SEQ ID NO:4, described hereinafter;

(b) hybridizes under non-stringent conditions to the vvh gene of *Vibrio vulnificus*; and (c) is labeled with a detectable marker.

In another embodiment, the above-described objects of the present invention have been met by a method for detecting the presence of pathogenic strains of *Vibrio vulnificus* in a sample comprising an unknown nucleic acid, comprising (1) hybridizing, under non-stringent conditions, a labeled nucleic acid hybridization probe with the unknown nucleic acid in the sample, wherein the labeled nucleic acid hybridization probe;

(a) consists of a total nucleotide sequence of from about 15 to 100 bases in length; wherein at least 15 bases of the total nucleotide sequence corresponds to a polynucleotide sequence selected from the group consisting of SEQ ID NO:1; SEQ ID NO:2; SEQ ID NO:3 and SEQ ID NO:4;

(b) hybridizes under non-stringent conditions to the vvh gene of *Vibrio vulnificus*; and (c) is labeled with a detectable marker; and (2) assaying for cross-hybridization of the labeled nucleic acid hybridization probe with the unknown nucleic acid in the sample so as to detect the presence of pathogenic strains of *Vibrio vulnificus* in the sample.

These and other objects of the present invention will be apparent from the detailed description of the invention provided hereinafter.

BRIEF DESCRIPTION OF THE DRAWINGS

FIG. 1 shows SEQ ID NO:1 and SEQ ID NO:2 DNA nucleotide sequences.

FIG. 2 shows SEQ ID NO:3 and SEQ ID NO:4 DNA nucleotide sequences.

DETAILED DESCRIPTION OF THE INVENTION

Previously unknown nucleic acid hybridization probes, specific for pathogenic strains of *Vibrio vulnificus*, have been discovered in the present invention. Based on the selection criteria described below, six regions (Regions 1-6) within the two open reading frames of the *V. vulnificus* 3.4 kb HindIII/EcoRI fragment were selected, as described below, to provide sequences having high selectivity and specificity as deoxynucleotide hybridization probes. However, of the six regions within the two open reading frames so selected, it was unexpectedly discovered that only two (Regions 2 and 6) provide nucleic acid probes that are particularly preferred and commercially suitable and useful, and that have a high degree of sensitivity and specificity, thereby providing diagnostically suitable hybridization probes for the detection of pathogenic strains of *V. vulnificus*. Furthermore, it was discovered that one of the above six regions provided an nucleic acid probe which detected only 86% of 28 *V. vulnificus* laboratory strains tested. Thus, the analysis and selection criteria initially used did not predictively suggest which regions of the two open reading frames would provide suitable nucleic acid hybridization probes for pathogenic strains of *V. vulnificus* is to distinguish such from non-pathogenic strains of *V. vulnificus*.

Hence, it has been unexpectedly discovered that the presumed selection criteria were unpredictable for providing preferred probes.for detecting pathogenic strains of *V. vulnificus*.

Preferred probes were discovered, however, for pathogenic strains of *Vibrio vulnificus*, wherein such probes (a) consist of a total nucleotide sequence of from about 15 to 200 bases in length; wherein at least 15 bases of the total nucleotide sequence is a segment of a polynucleotide sequence selected from the group consisting of SEQ ID NO:1, SEQ ID NO:2; SEQ ID NO:3 and SEQ ID NO:4;

(b) hybridizes under non-stringent conditions to the vvh gene of *Vibrio vulnifcus*; and (c) is labeled with a detectable marker.

Selection of expected suitable sequences to be used for nucleotide hybridization probes specific for *V. vulnificus*, which however were found to not provide expected suitability, was based on the presence of one or more of the following characteristics which are well known to provide some expectation of probe specificity:

(1) moderate/high guanine/cytosine (GC) ratios, (2) lack of internal repeats, (3) regions of homology with the *Vibrio cholera* hemolysin gene, (4) regions within major hydrophobic or hydrophilic segments, and (5) sequences corresponding to portions of open reading frames.

References herein to the portions of the above 3.4 kb HindIII/EcoRI fragment correspond to the numbered sequence of FIG. 2 presented in Yamamoto et al *Infection and Immunity*, 58:2706–2709 (1990), the contents of which are herein incorporated by reference.

Region 1 (corresponding to nucleotides 565 to 586 of the 3.4 kb fragment mentioned above) was selected based on a high (60%) GC content, being within a vvhB open reading frame, and some lack of internal repeats.

Region 2 (corresponding to nucleotides 891 to 914 of the 3.4 kb fragment mentioned above) was selected based on a high (60%) GC content, lack of internal repeats, and within the vvhA reading frame.

Region 3 (corresponding to nucleotides 988 to 1011 of the 3.4 kb fragment mentioned above) was selected based on a relatively high (50%) GC content, homology to the Cholera hemolysin gene, and some lack of internal repeats.

Region 4 (corresponding to nucleotides 1147 to 1164 of the 3.4 kb fragment mentioned above) was selected based on major hydrophobic or hydrophilic regions and being within the vvhA reading frame.

Region 5 (corresponding to nucleotides 1671 to 1695 of the 3.4 kb fragment mentioned above) was selected based on a high (68% GC) content and being within the vvhA reading frame.

Region 6 (corresponding to nucleotides 1857 to 1880 of the 3.4 kb fragment mentioned above) was selected based on a high (58%) GC content, lack of internal repeats and being within the vvhA reading frame.

Since no correlation was particularly apparent between the suitability of the probes and the above-described characteristics, routine experimentation would not predictably provide suitable regions for probes of the present invention.

Using the above-described regions, Regions 2 and 6 were found to contain sequences suitable for probes of the present invention (e.g., as probes comprising SEQ ID NO:1, SEQ ID NO:2, SEQ ID NO:3, and SEQ ID NO:4) for use in nucleic acid hybridization, as a means of detecting the presence of a nucleotide sequence specific and sensitive for pathogenic strains of *V. vulnificus*.

Hybridization can be carried out in solution by well-known methods (see, generally, for probe design, hybridization, and stringency conditions, e.g., Ausubel et al., eds. *CURRENT PROTOCOLS IN MOLECULAR BIOLOGY,* Wiley Interscience, New York, sections 6.3 and 6.4 (1988,1990), and Loggins et al, *Cancer Res.,* 39:545 (1979) ) or on a solid support (see e.g., Maniatis et al, *MOLECULAR CLONING: A LABORATORY MANUAL,* Cold Spring Harbor Laboratory, Cold Spring Harbor, N.Y. (1982) or in situ (see e.g., Brigati et al. Virol., 126:32 (1893) and Beckmann et al, *J. Med. Virol.,* 16:265 (1895), the contents of each of which are herein incorporated by reference).

Examples of probe labeling and detection include radioisotope labeling, such as end-labelling with [$\delta$-$^{32}$P] ATP using T4 polymerase kinase (See, e.g., Maniatis, supra, and Miliotus et al, *J. Clin. Micro.* 27:1667-1670 (1989), the contents of each of which are herein incorporated by reference. Other examples include non-radioisotope labeling, such as incorporation of a modified base directly linked to a detectable marker (see, e.g., Jablonski et al., *Nucleic Acids Res.* 14:6115-6128 (1986) and Olive et al, *J. Clin. Micro.* 27:1667-1670 (1989) the contents of each of which are herein incorporated by reference).

In the context of the present invention, "stringent" hybridization conditions refer to hybridization at a temperature of about 10°-25° C. below the melting temperature of a perfectly base-paired double stranded DNA having a base composition equal to that of the vvh gene or fragments thereof. Also in the context of the present invention, "non-stringent" hybridization conditions refers to hybridization at a temperature of at least about 350C below the melting temperature of a perfectly base-paired double stranded DNA having a base composition equal to that of the vvh gene or fragments thereof.

Hybridization can be carried out, on a solid support using a variety of different procedures. The specific procedure employed is not critical to the present invention. One such procedure involves purifying the unknown DNAs or RNAs, immobilizing such on a solid support in single-stranded form, followed by hybridization with a vvh specific nucleic acid probe which has been labeled with a marker (for example, as described in Maniatis, supra, miliotus, supra, and Olive, supra. )

Hybridization in situ can be performed, for example, on glass slides and the end result of the procedure is viewed through a microscope. In this procedure, the DNA or RNA is not purified from the cells but is left with all of the other cellular components on the slide. (See e.g., Brigatti, supra and Beckman, supra.)

When employing vvh RNA as a hybridization probe for detecting vvh DNA in an unknown sample of DNA, it is preferable that the DNA-RNA hybrids be formed after first hybridizing under stringent hybridization conditions, followed by treatment with pancreatic RNaseA (about 20 μg/ml in 50 mM NaCl (pH 7.0) at room temperature (about 20°-300° C.), followed by washing under stringent hybridization conditions.

Nucleic acid probes as DNA probes or RNA probes comprising SEQ ID NO:1, SEQ ID NO:2, SEQ ID NO:3 and SEQ ID NO:4, described hereinafter, are useful as nucleic acid hybridization probes of a practical length which are specific and selective for vvh DNA or RNA when labelled with a radioactive marker such as $^{32}$P, $^{14}$C, $^{3}$H, $^{125}$I, or $^{35}$S.

In the context of the present invention, the term "DNA" as comprising DNA probes refers to deoxyribonucleic acids comprising bases selected from the group consisting of (1) naturally occurring modified or unmodified bases or (2) synthetically modified or unmodified bases. Naturally occurring bases can include, e.g., unmodified bases include thymidine, guanidine, adenine, cytosine and deoxyuridine. Naturally occurring or synthetically modified bases include, e.g., 4-acetylcytidine, 5-(carboxyhydroxylmethyl)uridine, 2'-methylcytidine, 5-carboxymethylaminomethyl-2-thioridine, 5-carboxymethylaminomethyluridine,2'-O-methylpseudouridine, beta, D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta, D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl) carbamoyl) threonine, N-((9-beta-D-ribofuranosylpurine-6-yl)N-methylcarbamoyl) threonine, uridine-5-oxyacetic acid methylester, uridine-5-oxyacetic acid (v), wybutoxosine, pseudouridine, queosine, 2-thiocytidine, 5-methyl-2-thiouridine, 5-methyluridine, N-((9-beta-D-ribofuranosylpurine-6-yl)carbamoyl)threonine, 2'-O-methyl-5-methyluridine, 2'-O-methyluridine, wybutosine, (acp3)u. Additionally the term DNA includes all known types of DNA, e.g., RDNA, CDNA, genomic DNA, or ZDNA, as single stranded, double stranded or triple stranded, linear or circular.

In the context of the present invention, the term "RNA" as comprising RNA probes refers to ribonucleic acids comprising bases selected from the group consisting of (1) naturally occurring modified or unmodified bases or (2) synthetically modified or unmodified bases. Naturally occurring bases can include, e.g., unmodified bases include guanidine, adenine, cytosine and uridine. Naturally occurring or synthetically modified bases include, e.g., 4-acetylcytidine, 5-(carboxyhydroxylmethyl)uridine, 2'-O-methylcytidine, 5-carboxymethylaminomethyl-2-thioridine, 5-carboxymethylaminomethyluridine, dihydrouridine, 2'-O-methylpseudouridine, beta, D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta, D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, (acp3)u.. Additionally the term RNA includes all known types of RNA, e.g., rRNA, mRNA, hnRNA, TRNA or anti-sense RNA, as single stranded, double stranded or triple stranded, linear or circular.

The Vvh specific DNA nucleic acid probes of the present invention can be radioactively labelled, e.g., by "nick-translation" by well known means, as described in, e.g., in Rigby et al, *J. Mol Biol.* 113:237 (1977) and e.g., by T4 DNA polymerase replacement synthesis as described in, e.g., Deen et al. *Anal Biochem.* 135:456 (1983).

Vvh specific RNA nucleic acid probes of the present invention can be labelled with a radioactive marker by in vitro transcription as described in, e.g., Davanloo et al. *Proc. Natl. Acad. Sci, USA* 81:2035 (1984). Since RNA polymerases can utilize labelled precursors, it is possible to synthesize labelled RNA by this method so as to prepare vvh RNA probes for the detection of vvh DNA or RNA. Labelled precursors which can be used to synthesize labelled RNA include precursors containing radioactive markers such as $^{32}P$, $^{14}C$, $^{3}H$, $^{125}I$, or $^{35}S$.

DNA or RNA nucleic acid probes are also useful as nucleic acid hybridization probes for vvh DNA or RNA when labelled with a non-radioactive marker such as biotin, an enzyme or fluorescent group. Biotin acts as a hapten-like group and can be bound to DNA or RNA and detected by binding an avidin-conjugated enzyme or streptavidin-conjugated enzyme to the biotin, followed by washing to remove non-specifically bound enzyme. Upon addition of appropriate substrates for the enzyme, the conversion of the substrate to a colored product can be detected (see e.g., Leary et al, *Proc Acad. Sci. USA.* 80:4045 (1983)). Examples of such enzymes include alkaline phosphatase and horseradish peroxidase.

In addition, fluorescent molecules, such as fluorescein and rhodamine can be chemically conjugated to avidin or streptavidin and employed as non-radioactive markers.

Alternatively, the above-described enzymes or fluorescent molecules can be chemically conjugated directly to the vvh-encoding DNA or RNA nucleic acid probes as described in, e.g., Renz *EMBO J.,* 6:817 (1983), and used in this manner as hybridization probes.

The thus labelled vvh DNA or vvh RNA nucleic acid probes can be used as described above for hybridization with an unknown sample of DNA or RNA, particularly an unknown sample comprising DNA or RNA derived from human or animal blood, to determine if the sample contains vvh -encoding DNA or RNA.

The unknown sample comprising DNA or RNA, in addition to being derived from blood, can be derived from animal sources, such as animal tissues, such as a throat, skin or lung tissue, and other animal fluids, such as sputum, ear fluids, stool, urine or a wound culture. Additional samples can be environmental samples, such as water, shellfish meat culture, earth, rock and the like.

The unknown sample of DNA or RNA can be obtained by, for example, by taking a blood, stool or wound sample, by scraping the throat or by swabbing the throat to obtain exfoliated cells and cultured to provide detectable levels of *V. vulnificus* nucleic acid. In addition, the unknown sample comprising DNA or RNA can be obtained from bacterial cells in which DNA from an animal tissue has been cloned using well known means as described, e.g. in Maniatis et al, *MOLECULAR CLONING: A LABORATORY MANUAL,* Cold Spring Harbor Laboratory, Cold Spring Harbor, N.Y. (1982); and Gissman *Cancer Surv.* 3:161-181 (1984).

Additionally, environmental samples can be water samples as salt water, fresh water, and brackish water obtained from rivers, streams lakes, marshes or other bodies of water, ground water, piped water, filtration or purification plants effluents, soil, earth, and rock. Plants, crops or animals can also be animal sources, especially aquatic animals, such as shellfish, fish or marine mammals or water in which such animals are found. Marine mammals can include whales porpoises and dolphins. Shellfish can include, but are not limited to, oysters, clams, mussels, crabs, lobster, crayfish, and the like. Animals include, e.g., terrestrial and aquatic animals. Terrestrial animals can include mammals, such as livestock, domestic animals and humans. Livestock can include cows, horses, pigs, goats, and sheep. Domestic animals can include, e.g., cats, dogs, and horses.

Samples can also include those from a human source, such as a human tissue or a body fluid. Human tissues can include, e.g., blood, throat, skin, lung, organ, muscle, and bone. Body fluids can include, e.g., sputum, ear fluids, stool, urine, vaginal fluid, uterine fluid, and amniotic fluid.

Other sources of samples include, e.g., environmental sources, such as salt water including water from salt marshes, bay water, and ocean water. Fresh water samples can be obtained from river water, stream water, lake water, marsh water, ground water, and piped water. Brackish water samples can include, e.g., salt marsh water, estuary water and river water.

In the methods of the present invention, assaying for cross-hybridization can be carried out by assaying for the presence of radioactive or non-radioactive marker associated with double-stranded nucleic acid hybrids. The methods for determining whether a specific marker is present will depend upon the marker employed and are well-known in the art.

When the amount of unknown RNA or DNA in the unknown sample may be insufficient to provide detectable hybridization using the above-described probes and methods of the present invention for detecting pathogenic strains of *Vibrio vulnificus*, an additional preliminary step may be employed to produce samples suitable for the detecting methods of the present invention. Such a step would include a known DNA/RNA amplification method to amplify one or more sequences of the vvh gene that bind a hybridization probe of the present invention. For example, amplification primer sequences comprising polynucleotides complimentary to sequences adjacent to hybridizing portions of the vvh gene can be used to provide sufficient copies of the hybridizing portions, in order to allow detection of the vvh gene, according to methods of the present invention. Known DNA/RNA amplification methods include, e.g., PcR ® (see, e.g., U.S. Pat. Nos. 4,683,195 and 4,683,202, issued to Cetus Corporation), Ligase chain reaction (see, e.g., Landegren, et al., Science 241: 1077-1080, 1988), NASBA ® (see European patent Application Nos. EP-329,822 and EP-113,948, corresponding to U.S. patent application Ser. No. 07/211,384), and Q-beta replicase (see, e.g., Kramer et al, *Biotechnology* 6:1197 (1988), the contents of each of which are herein incorporated by reference).

Thus, another embodiment of the present invention additionally includes initial amplification of sequences in a sample of interest to produce larger amounts of the vvh gene for hybridization to nucleic acid probes of the present invention, followed by hybridizing and detecting the presence of the vvh gene in a sample of unknown RNA or DNA.

The particular size of the vvh DNA or vvh RNA probes which can be employed as hybridization probes in the present invention can be, for example, from about 15 to 200 bases or base pairs, depending on whether single stranded bases or double stranded (base pairs) probes are employed, preferably about 15 to 40 bases or base pairs, and more preferably about 15 to 30 base pairs. When using double-stranded DNA or RNA, the DNA or RNA must be denatured prior to carrying out hybridization.

Vvh -specific DNA or RNA nucleic acid probes can be obtained by synthetically manufacturing such using any of the commercially available DNA synthesizing apparatus or by well known chemical methods using the vvh DNA sequence which can be determined by known means (Sanger et al, *Proc. Natl. Acad. Sci. USA.* 74:5363 (1977)).

The following examples are given to further illustrate the present invention and are in no way intended to limit the scope of the present invention. Unless otherwise indicated, all parts, percents, ratios and the like are by weight.

In the following examples, probes specific for pathogenic strains of *V. vulnificus* were, in one alternative method, end-labeled, according to well known procedures, e.g., See Maniatis et al Supra, pg. 115-129 and Ausubel et al, supra, at §6.

For the following examples, the following solutions were used:

Lysis solution (0.5 M NAOH, 1.5M NaCl) was autoclaved and stored at room temp. Amonium acetate buffer (2M) was autoclaved and stored at room temp. Standard Saline Citrate (SSC) buffer (0.15M NaCl, 0.015M Na Citrate, pH 7.0, as a 20x solution) was diluted in autoclaved dH$_2$O prior to use and stored at room temperature. Proteinase K solution (40 μg/ml of proteinase K) was prepared from a ProK stock solution (20 mg/ml ProK in SSC stored at −20° C.) immediately prior to each use. Hybridization Buffer (0.5% bovine serum albumin (BSA), 1.0% Lauryl sulfate (SDS), and 0.5% Polyvinylpyrrolidone (PVP)) was filtered (0.45 micron, Nalgene) and stored at 4° C. for no longer than 2 days. The buffer solution was prewarmed to 50° C. prior to use.

SSC/Lauryl Sulfate (SSC/SDS) (1% w/v) was stored at room temp. NBT (50 mg/ml) and BCIP (50 mg/ml) were prepared according to known procedures and stored at 4° C. in the dark. Diethanolamine (DEA) Buffer was prepared as listed below and stored at 4° C.

| DEA | 19.3 ml |
|---|---|
| 2M MgCl$_2$ | 5.0 ml |
| NaN$_3$ | 0.4 g |
| H$_2$O | 2.0 liters |
| HCl (pH 9.5) | about 1.4 ml |

Prehybridization/hybridization solution (6X Standard Saline Citrate (SSC), 5X Denhardt's solution; 1.0 mm EDTA (pH 8.0), salmon sperm (100 μg/ml) and distilled water); Standard Saline Citrate (1X) (SSC 1X) (0. 15M NaCl and 0. 015M Na Citrate); and Denhardt's Solution (0.2% Ficoll (w/v), 0.2% Polyvinylpyrrolidone (w/w), and 0.2% bovine serum albumin (w/v)).

EXAMPLE 1

Sequence Analysis

The DNA sequence (as described in Yamamoto et al *Infect and Immun.* 58:2706-2709 (1990), the contents of which are herein incorporated by reference) of the *V. vulnificus* 3.4 kb HindIII/EcoRI fragment from strain EDL-174 was analyzed for evidence of internal repeats, and the BIONET database was screened for homologous sequences. Both BIONET and the Pustell Sequence Analysis programs were used to identify hydrophobic and hydrophilic regions; GC ratios were calculated using the Pustell programs.

No significant repeats or other features of interest were found in the analysis of the primary structure of the 3.4 kb fragment. While there were varying degrees of homology with other sequenced genes, none appeared to be significant. One 8 amino acid sequence was shared by the *V. vulnificus* and *V. cholera* hemolysins (base pairs. 244-267 in FIG. 3 of Yamamotol, et. al. However, there were differences in the underlying nucleotide structure of this region in the two hemolysins.

In examining the hydropathy plots, the cytotoxin structural gene (the second open reading frame) was substantially hydrophilic. There was an initial hydrophobic region corresponding to the location of the signal peptide. There was a very strong hydrophilic region centering on bp 450; this may represent a major epitope or antigen binding site. The protein encoded by the first open reading frame, in contrast, is relatively hydrophobic. There were two particularly strong hydrophobic regions (i.e., 200-270 bp and 499-560 bp) which may represent membrane-spanning segments.

EXAMPLE 2

Selection/Synthesis of Nucleic acid Probes

Six regions within the two open reading frames described in Example 1 above were selected for construction of synthetic probes. Selection was based on moderate/high GC ratios, lack of internal repeats, regions of homology with the *V. cholera* hemolysin, regions within major hydrophobic or hydrophilic segments, and spacing within open reading frames. References below to these regions correspond to the numbered sequence of FIG. 2 presented in Yamamoto et al *Infection and Immunity,* 58:2706-2709 (1990), the contents of which are herein incorporated by reference.

Region 1 as probe 1 (corresponding to nucleotides 565 to 586 of the 3.4 kb fragment mentioned above) was selected based on a high (604) GC content, being within a vvhB open reading frame, and some lack of internal repeats.

Region 2 as probe 2 (SEQ ID NO:1, corresponding to nucleotides 891 to 914 of the 3.4 kb fragment mentioned above) was selected based on a high (60%) GC content, lack of internal repeats, and within the vvhA reading frame.

Region 3 as probe 3 (corresponding to nucleotides 988 to 1011 of the 3.4 kb fragment mentioned above) was selected based on a relatively high (50%) GC content, homology to the Cholera hemolysin gene, and some lack of internal repeats.

Region 4 as probe 4 (corresponding to nucleotides 1147 to 1164 of the 3.4 kb fragment mentioned above) was selected based on major hydrophobic or hydrophilic regions and being within the vvhA reading frame.

Region 5 as probe 5 (corresponding to nucleotides 1671 to 1695 of the 3.4 kb fragment mentioned above) was selected based on a high (68% GC) content and being within the vvhA reading frame.

Region 6 as probe 6 (SEQ ID NO: 2 corresponding to nucleotides 1857 to 1880 of the 3.4 kb fragment mentioned above) was selected based on a high (58%) GC content, lack of internal repeats and being within the vvhA reading frame.

The above sequences were synthesized according to known methods on an Applied Biosystems Model 380B DNA synthesizer, and purified using an Applied Biosystems Purification Cartridge.

SEQ ID NO:3 and SEQ ID NO:4 are the RNA sequences corresponding to SEQ ID NO:1 and SEQ ID NO:2, respectively,

EXAMPLE 3

Testing of Nucleic acid Probes

I) Laboratory Strains

In initial hybridization experiments, all six probes and the original 3.4 kb cloned cytotoxin gene were used to screen a collection of 100 bacterial strains from laboratory strain collection. "Standard" hybridization conditions were used, as outlined herein.

Filter Preparation. Using sterile toothpicks, bacterial colonies to be tested were inoculated to L agar or Nutrient Agar with NaCl and incubated overnight at room temp.

Preparation of Colony Blots to screen bacterial strains with nucleic acid probes. 545-type filters were layered on top of colonies on a plate for several minutes. Filters were removed and placed on Whatman #3 filters soaked with 5.0 ml of lysing solution (0.5N NAOH, 1.5N NaCl) in a glass petri dish. Filters were then steamed for 3-5 minutes in an open autoclave. 541-type filters were placed on fresh Whatman #3 filters with about 35 ml of lysing solution were added and incubated for 2 minutes at room temperature. The filters were transferred to #3 filter paper that had been soaked with neutralizing solution (1.0 M Tris pH 7.0, 2.0 M NaCl) for 5 minutes, and then air dried.

Modifications to the above procedure included the following. As an alternative to the use of 35 ml of the lysing solution, 541-type filters were placed on fresh Whatman #3 filters with 4.0 ml of ammonium acetate. The filters were then transferred to a second petri dish and incubated for 5 minutes at room temperature. The filters were then placed in petri dishes with excess 2X Standard Saline Citrate (SSC) to rinse. Then, the rinse was repeated and the filters were air dried.

Proteinase K treatment. (optional) Filters were optionally incubated in proteinase X solution (50ml) for 30 minutes at 42° C. in a plastic container. Up to about 10 filters were incubated at a time. The filters were washed 2 times in SSC (50ml) for 10 minutes at room temperature with shaking at 50rpm. A maximum of 5 filters/bag were washed with 10-30 ml of buffer. The buffer was poured off from the bag. Prewarmed (50° C.) hybridization buffer and AP probe (2 $\mu$l/filter) were mixed in a plastic tube and added to the bag with filter(s) and incubated for 1 hour at 50° C. with shaking. In a plastic container, the filters were washed 3 times for 5 minutes in SSC at room temperature with shaking.

Hybridization of nucleic acid probes to nucleic acid bound to the filters prepared as described above was carried out using the following solutions:

The filters were placed in bags with prehybridization solution (5.0 ml/filter) and incubated at 37° C. for 5 and $\frac{1}{2}$ hours, and then incubated at 42° C. for $\frac{1}{2}$ hour. Hybridization solutions containing labeled probe ($10^7$ cpm) were added, and the filters/solution incubated at 42° C. overnight. The filters were then rinsed briefly in 6X SSC (60° C.) and then washed for 1-hour in 6X SSC at 60° C.; followed by transfer to fresh 6X SSC (65° C.) and washing for one hour. Then, the filters were rinsed briefly in 2X SSC at room temperature. Finally, the filters were air dried, and exposed to autoradiographic film overnight at −70° C.

Modifications to the above hybridization procedure included: Prehybridization for 3 hours at 37° C. instead of 5$\frac{1}{2}$ hours at 37° C.

Color development. In petri dish, DEA buffer (10 ml) was mixed with NBT (40$\mu$l) and BCIP (33$\mu$l). Filters (5 or less) were added to the dish and incubated at room temperature in the dark with shaking. Development was checked every half hour and was usually complete after 1 hour. Tap water was added to stop development. Developed filters were dried and stored in acetate holders.

Using the above procedure, Probe 2 (SEQ ID NO: 1) and probe 6 (SEQ ID NO:2) had superior sensitivity and specificity to the other oligonucletide probes (1, 3, 4 and 5) and was also superior over the use of the 3.4 kb fragment, due to its short length and lack of need to cleave from a plasmid prior to each use, as required by the 3.4 kb fragment. However, there was a clear decrease in sensitivity with probe 1: a positive result was obtained with only 24 (864) of the 28 *V. vulnificus* tested. Furthermore, probes 3, 4 and 5 were less suitable than probes 2 and 6. Thus, of the six probes expected to have high level of specificity and sensitivity, only probes 2 and 6 were found to have such a level.

II) Environmental Strains

A collection of 226 environment-1 Vibrio strains (see Table I, below) were using synthetic probes 2 and 6 and the originally cloned 3.4 kb cytotoxin gene as described above. Strains were provided by Jerri Misselli from the FDA North East Technical Service Unit in Rhode Island. Probe 2 had a sensitivity of 100% and a specificity of 98.6% when compared with results obtained using cloned 3.4 kb fragment; probe 6 has a sensitivity of 99.3% and a specificity of 100%.

TABLE I

| LABORATORY STRAINS USED IN SCREENING SYNTHETIC PROBES | |
|---|---|
| | # isolates |
| *Vibrio vulnificus* | 28 |

TABLE I-continued
LABORATORY STRAINS USED IN SCREENING SYNTHETIC PROBES

|  | # isolates |
|---|---|
| V. cholerae | 10 |
| V. parahaemolyticus | 10 |
| V. alginolyticus | 1 |
| V. damsela | 1 |
| V. fluvialis | 1 |
| V. furnissii | 1 |
| V. harveyii | 1 |
| V. hollisae | 1 |
| V. metschnikovii | 1 |
| V. mimicus | 1 |
| Salmonella spp | 10 |
| Serratia marcescens | 5 |
| Citrobacter diversus | 5 |
| E. coli (EPEC) | 5 |
| E. coli (ETEC) | 5 |
| Shigella sonnei | 2 |
| S. boydii | 1 |
| S. flexneri | 1 |
| S. dysenteriae | 1 |

EXAMPLE 4

Identification of V. vulnificus using alkaline phosphatase gene probe

Using the above-described procedures, alkaline phosphatase labeled probe 6 was used to detect the presence of Vibrio vulnificus, as compared to detection using known biochemical procedures and, additionally, as compared to detection using a $^{32}$P-labeled 3.4 kb fragment, as described above.

Oysters were collected, homogenized in PBS, and plated on a enrichment medium. Presumptive Vibrio vulnificus strains were identified by typical biochemical characterization. These strains were further assayed for homology to both a $^{32}$P labeled, 3.4 kb probe and an alkaline phosphatase-labeled probe 6, according to the methods of the above Examples, and analyzed for their fatty acid (FA) profile. Only 66% of presumptive pathogenic Vibrio vulnificus (n=61) strains were confirmed by the $^{32}$P-3.4 kb probe and FA analysis; however, there was 100% correlation among the results for identification of Vibrio vulnificus by alkaline phosphatase probe 6 and the presumptive pathogenic strains. The mean number of Vibrio vulnificus in oysters based on confirmation by all methods was 2000/g of oyster. These data indicate that the alkaline phosphatase probe provides a superior means of identifying in oysters, as compared to the use of conventional biochemical characterization and the use of the 3.4 kb probe, or a combination thereof.

Other objects, features and advantages of the present invention will become apparent to those skilled in the art from the above detailed description and Examples of the present invention. It should be understood, however, that the description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. A nucleic acid hybridization probe specific for pathogenic strains of *Vibrio vulnificus,* wherein said probe
   (a) consists of a total nucleotide sequence of from about 15 to 200 bases wherein; at least 15 bases of said total nucleotide sequence corresponds to a polynucleotide sequence selected from the group consisting of SEQ ID NO: 1, SEQ ID NO: 2, SEQ ID NO:3 and SEQ ID NO:4;
   (b) hybridizes under non-stringent conditions to the vvh gene of *Vibrio vulnificus*; and
   (c) is labeled with a detectable marker.

2. The hybridization probe as claimed in claim 1, wherein said detectable marker is a radioactive marker.

3. The hybridization probe as claimed in claim 2, wherein said detectable marker is a radioactive marker selected from the group consisting $^{32}$P, $^{14}$C, $^{3}$H, $^{125}$I and $^{35}$S.

4. The hybridization probe as claimed in claim 1, wherein said detectable marker is a non-radioactive marker.

5. The hybridization probe as claimed in claim 1, wherein said detectable marker is a non-radioactive marker selected from the group consisting of biotin, an enzyme and a fluorescent molecule.

6. The hybridization probe as claimed in claim 5, wherein said detectable marker is an enzyme.

7. The hybridization probe as claimed in claim 6, wherein said enzyme is selected from the group consisting of alkaline phosphatase and horseradish peroxidase.

8. The hybridization probe as claimed in claim 5, wherein said detectable marker is a fluorescent molecule.

9. The hybridization probe as claimed in claim 8, wherein said fluorescent molecule is selected from the group consisting of fluorescein and rhodamine.

10. The hybridization probe as claimed in claim 5, wherein said detectable marker is biotin.

11. The hybridization probe as claimed in claim 1, wherein said polynucleotide sequence (a) is selected from the group consisting of SEQ ID NO:1 and SEQ ID NO:2.

12. The hybridization probe as claimed in claim 11, wherein said polynucleotide sequence consists of SEQ ID NO:1.

13. The hybridization probe as claimed in claim 11, wherein said polynucleotide sequence consists of SEQ ID NO:2.

14. The hybridization probe as claimed in claim 1, wherein said polynucleotide sequence (a) is selected from the group consisting of SEQ ID NO:3 and SEQ ID NO:4.

15. The hybridization probe as claimed in claim 14, wherein said polynucleotide sequence consists of SEQ ID NO:3.

16. The hybridization probe as claimed in claim 14, wherein said polynucleotide sequence consists of SEQ ID NO:4.

17. A method for detecting the presence of pathogenic strains of *Vibrio vulnificus* in a sample comprising an unknown nucleic acid, comprising
   (1) hybridizing, under non-stringent conditions, a labeled nucleic acid hybridization probe in said sample with said unknown nucleic acid in said sample, wherein the labeled nucleic acid hybridization probe;
   (a) consists of a total nucleotide sequence of from about 15 to 200 bases wherein; at least 15 base pairs of said total nucleotide sequence corresponds to a polynucleotide sequence selected from the group consisting of SEQ ID NO:1, SEQ ID NO:2, SEQ ID NO:3 and SEQ ID NO:4;
   (b) hybridizes under non-stringent conditions to the vvh gene of *Vibrio vulnificus* ; and
   (c) is labeled with a detectable marker; and
   (2) assaying for cross-hybridization of the labeled nucleic acid hybridization probe with said unknown nucleic acid in said sample so as to detect the presence of pathogenic strains of *Vibrio vulnificus* in said sample.

18. The method as claimed in claim 17, wherein said detectable marker is a radioactive marker.

19. The method as claimed in claim 17, wherein said detectable marker is a radioactive marker selected from the group consisting of $^{32}$P, $^{14}$C, $^{3}$H, $^{125}$I and $^{35}$S.

20. The method as claimed in claim 17, wherein said detectable marker is a non-radioactive marker.

21. The method as claimed in claim 20, wherein said detectable marker is a non-radioactive marker selected from the group consisting of biotin, an enzyme and a fluorescent molecule.

22. The method as claimed in claim 21, wherein said marker is an enzyme.

23. The method as claimed in claim 22, wherein said enzyme is selected from the group consisting of alkaline phosphatase and horseradish peroxidase.

24. The method as claimed in claim 21, wherein said marker is a fluorescent molecule.

25. The method as claimed in claim 24, wherein said fluorescent molecule is selected from the group consisting of fluorescein and rhodamine.

26. The method as claimed in claim 21, wherein said marker is biotin.

27. The method as claimed in claim 17, wherein said unknown sample is obtained from blood or is nucleic acid derived from a tissue of said human which has been cloned into a cloning vector.

28. The method as claimed in claim 17, wherein at least any one of said cross-hybridizations produces DNA-DNA hybrids.

29. The method as claimed in claim 517, wherein at least any one of said cross-hybridization produces DNA-RNA hybrids.

30. The method according to claim 17, wherein said sample is derived from an animal source.

31. The method according to claim 30, wherein said animal source is selected from the group consisting of aquatic animals and terrestrial animals.

32. The method according to claim 31, wherein said aquatic animals are selected from the group consisting of shellfish, fish and aquatic mammals.

33. The method according to claim 32, wherein said shellfish are selected from the group consisting of oysters, clams, mussels, crabs, lobsters, and crayfish.

34. The method according to claim 31, wherein said terrestrial animals are mammals.

35. The method according to claim 34, wherein said mammals are selected from the group consisting of livestock, domestic animals and humans.

36. The method according to claim 35, wherein said livestock is selected from the group consisting of cows, horses, pigs, goats, and sheep.

37. The method according to claim 35, wherein said domestic animals are selected from the group consisting of cats, dogs, and horses.

38. The method according to claim 35, wherein said human source comprises a human tissue or a body fluid.

39. The method according to claim 38, wherein said tissue is selected from the group consisting of blood, throat, skin, lung, organ, muscle, and bone.

40. The method according to claim 38, wherein said body fluid is selected from the group consisting of sputum, ear fluids, stool, urine, vaginal fluid, uterine fluid, and amniotic fluid.

41. The method according to claim 17, wherein said sample is derived from an environmental source.

42. The method according to claim 41, wherein said environmental source is selected from a group consisting of water, earth, and rock.

43. The method according to claim 42, wherein said water sample is selected from a group consisting of salt water, fresh water, and brackish water.

44. The method according to claim 43, wherein said salt water is selected from the group consisting of salt marshes, bay water, and ocean water.

45. The method according to claim 43, wherein said fresh water sample is selected from the group consisting of river water, stream water, lake water, marsh water, ground water, and piped water.

46. The method according to claim 43, wherein said brackish water sample is selected from the group consisting of salt marsh water, estuary water and river water.

* * * * *